US008829220B2

(12) United States Patent
Doppiu et al.

(10) Patent No.: US 8,829,220 B2
(45) Date of Patent: Sep. 9, 2014

(54) PROCESS FOR PREPARING DIENYL-RUTHENIUM COMPLEXES

(75) Inventors: Angelino Doppiu, Seligenstadt (DE); Andreas Rivas-Nass, Schriesheim (DE); Ralf Karch, Kleinostheim (DE); Roland Winde, Frankfurt (DE)

(73) Assignee: Umicore AG & Co., KG, Hanau-Wolfgang (DE)

( * ) Notice: Subject to any disclaimer, the term of this patent is extended or adjusted under 35 U.S.C. 154(b) by 594 days.

(21) Appl. No.: 12/995,537

(22) PCT Filed: May 30, 2009

(86) PCT No.: PCT/EP2009/003904
§ 371 (c)(1),
(2), (4) Date: Mar. 21, 2011

(87) PCT Pub. No.: WO2009/146870
PCT Pub. Date: Dec. 10, 2009

(65) Prior Publication Data
US 2011/0184203 A1 Jul. 28, 2011

(30) Foreign Application Priority Data

Jun. 2, 2008 (DE) .................. 10 2008 026 284

(51) Int. Cl.
*C07F 15/00* (2006.01)
*C07F 17/02* (2006.01)
(52) U.S. Cl.
CPC ............. *C07F 15/0046* (2013.01); *C07F 17/02* (2013.01)
USPC ........................................................ 556/136
(58) Field of Classification Search
CPC .............................. C07F 15/0046; C07F 17/02
USPC ........................................................ 556/136
See application file for complete search history.

(56) References Cited

U.S. PATENT DOCUMENTS

| | | | |
|---|---|---|---|
| 6,743,935 B2 | 6/2004 | Salzer et al. | |
| 7,012,150 B2 | 3/2006 | Sagae | |
| 7,435,484 B2 * | 10/2008 | Shinriki et al. | 428/670 |
| 7,619,093 B2 | 11/2009 | Meiere | |
| 2002/0103395 A1 | 8/2002 | Saito | |
| 2010/0028535 A1 | 2/2010 | Meiere | |
| 2010/0034971 A1 | 2/2010 | Gatineau et al. | |

FOREIGN PATENT DOCUMENTS

| | | |
|---|---|---|
| EP | 1 156 055 | 11/2001 |
| EP | 1 283 843 B1 | 3/2006 |
| EP | 1887102 A1 | 2/2008 |
| JP | 2002-220397 | 8/2002 |
| JP | 2004-067558 | 3/2004 |
| JP | 2006-241557 | 9/2006 |
| JP | 2010-513467 | 4/2010 |
| WO | 01/87901 A1 | 11/2001 |
| WO | 2006/044446 A2 | 4/2006 |

OTHER PUBLICATIONS

Bauer et al., Organometallics, vol. 19, No. 25, pp. 5471-5476 (2000).*
International Search Report for PCT/EP2009/003904 mailed Oct. 28, 2009.
Hajime Yasuda, et al., "Pentadienylmetal Compounds, Structural Analyses and Applications in Organic Synthesis", Journal of Organometallic Chemistry, 285, 1985, pp. 15-19.
Michel O. Albers, et al., "Chemistry of Cyclopentadlenyl-Ruthenium and -Osmlum Complexes . . . ",Organometallics, 5, 1986, pp. 2321-2327.
Paolo Pertici, et al., "A New Synthetic Method for the Preparation of Cyclo-olefin Ruthenium Complexes", Journal of Chemical Society, 1980, pp. 1961-1964.
Jörn Müller, et al., "Über die Synthese neutraler . . . ", Chemische Berichte Jahrg., 108, 1975, pp. 273-282.
Paolo Pertici, et al., "Improved Synthesis of Cyclo-olefin Complexes . . . Reduction", J.C.S. Chem. Comm., 1975, p. 846.
P. Pertici and G. Vitulli, "Cycloolefin Complexes of Ruthenium", Organometallic Compounds, 1983, pp. 176-181.
Lothar Stahl and Richard D. Ernst, "Synthesis and Characterization of Bis(pentadienyl) ruthenium Compounds", Organometallics, 2, 1983, pp. 1229-1234.
D.R. Wilson, L. Stahl and R.D. Ernst, "Bis(2,4-Dimethylpentadienyl) Complexes of thr Transition Metals", Organometallic Synthesis, 1986, pp. 136-141.
Geoffrey L.D. Ritchie, et al., "Molecular Quadrupole Moments, Magnetic Anisotropies, . . . Ruthenocene", J. Am. Chem. Soc., vol. 105, No. 16, 1983, pp. 5215-5219.
W.E. Newton and J.E. Searles, "Preparation of Some . . . Carbon Monoxide", Inorganica Chimica Acta, vol. 7, No. 3, 1973, pp. 349-352.
F.M. Lever and A.R. Powell, "Ammine Complexes of Ruthenium", J. Chem. Soc. (A), 1969, pp. 1477-1482.
T.J. Haas, "Investigations of Ruthenium (II) Sources . . . ", vol. 22, No. 2/3, 1992, pp. 227-245.

(Continued)

*Primary Examiner* — Porfirio Nazario Gonzalez
(74) *Attorney, Agent, or Firm* — Smith, Gambrell & Russell LLP

(57) ABSTRACT

The present invention relates to a single-stage process for preparing dienyl-ruthenium complexes of the formula Ru(+II)(dienyl)$_2$, wherein an Ru(II) starting compound of the formula Ru(X)$_p$(Y)$_q$ is reacted with a diene ligand in the presence of an inorganic and/or organic base in a single-stage process. Here, polar organic solvents, preferably mixtures of polar organic solvents with water, are used. The dienyl-ruthenium complexes prepared according to the invention are used as precursors for homogeneous catalysts, for producing functional coatings and for therapeutic applications.

20 Claims, No Drawings

(56) References Cited

OTHER PUBLICATIONS

James M. Nelson, et al., "Synthesis and Ring-Opening Polymerization . . . ", Angewandte Chemie, International Edition, vol. 33, No. 9, May 18, 1994, pp. 989-991.

James M. Nelson, et al., "Synthesis, Structure, and Polymerization Behavior", Organometallics, vol. 13, No. 9, Sep. 9, 1994, pp. 3703-3710.

Margaret A.L. Blackie and Kelly Chibale, "Metallocene Antimalarials: The Continuing Quest", Metal-Based Drugs, vol. 2008, article id 495123, 2008, pp. 1-10.

Pascal Pigeon, et al., "Selective Estrogen Receptor Modulators . . . Behavior", J. Med. Chem., vol. 48, No. 8, Apr. 21, 2005, pp. 2814-2821.

David N. Cox et al, "*Octadienediyi Dichlorides of Ruthenium(IV) as Synthetic Reagents..*," -J. Chem. Soc., Chem. Commun:; 1988; 951-953.

André Bauer et al, "*Efficient Synthesis of Ruthenium(II) $n^5$-Dienyi Compounds Starting from Di-µ-chlorodichloro-bis. . . .*", Organometallics 2000, 19, 5471-5476.

D. E. Bublitz et al, "*Ruthenocene*", Organic Syntheses, Coll. vol. 5, p. 1001 (1973), vol. 41, p. 96 (1961).

Richard D. Ernst, "*Metal-Pentadienyl Chemistry*", Acc. Chem. Res. 1985, 18, 56-62.

Michael O. Albers et al, "*Ruthenium and Osmium complexes containing cyclopentadienyl and related penta hapto dienyl ligands*", Coordination Chemistry Reviews, 79 (1987) 1-96.

Richard D. Ernst, "*Structural and Reactivity Patterns in Transition-Metal-Pentadienyl Chemistry*", Chem. Ref. 1988, 88, 1255-1291.

Tito Lumini et al, "*Synthesis, crystal structures, and solution dynamics of some mono(2,4-dimethylpentadienyl)ruthenium(II) complexes*", Journal of Organometallic Chemistry, 434 (1992) 363-385.

\* cited by examiner

PROCESS FOR PREPARING DIENYL-RUTHENIUM COMPLEXES

The present invention relates to a process for preparing dienyl-ruthenium complexes. For the purposes of the present invention, these compounds are organometallic ruthenium compounds in which the central Ru atom is bound in a sandwich-like fashion to two dienyl ligands. The complexes of the invention can be represented by the formula Ru (II)(dienyl)$_2$. The central Ru atom has the oxidation state +II in these. Such compounds are, when they contain open-chain dienyl ligands, also referred to as "open ruthenocenes".

Dienyl-ruthenium complexes, in particular the open ruthenocenes, are becoming increasingly important as precursors for homogeneous catalysts. These compounds are used, for example, for the asymmetric hydrogenation of olefinic hydrocarbons and are also used for producing functional coatings by means of thin film processes (for example by MOCVD (metal-organic chemical vapour deposition) or PVD (physical vapour deposition). Therapeutic applications of dienyl-Ru complexes are also being examined at present.

Various processes for preparing dienyl-ruthenium complexes are known from the literature. The preparative processes which have hitherto been customary start out from Ru (II), Ru (III) or Ru (IV) compounds. These are generally reacted with a large excess of the appropriate olefin, diene or dienyl salt, usually in the presence of a reducing agent.

A known method of preparing ruthenium-olefin complexes is the Fischer-Müller synthesis, in which a Ru (III) or Ru (II) compound is reacted with a Grignard reagent in the presence of a ligand (cf. J. Müller et al., *Chemische Berichte*, 1975, 108, pages 273-282). This method is difficult to reproduce and gives poor yields.

G. Vitulli, P Pertici et al. (*J.C.S. Chem. Comm.*, 1975, p. 846 and *Inorg. Synth*, 22, 1983, pp. 176-181) describe a process for preparing cyclic dienyl-ruthenium complexes, in which ruthenium(III) trichloride hydrate as starting material is reacted with a large (in general from 30- to 50-fold) excess of the appropriate ligand in the presence of an excess of zinc dust as reducing agent. Residues of zinc can remain and contaminate the product. Owing to the large excess of ligand or olefin, the product is additionally contaminated by polymeric or oligomeric substances. Owing to these disadvantages, the process is hardly suitable for industrial use.

R. D. Ernst et al. (*Organometallics* 1983, 2, pp. 1229-1234 and *Organometallic Synthesis*, 1986, pp. 136-141) describe a process for preparing bis(2,4-dimethyl-pentadienyl)ruthenium(II), viz. an open ruthenocene, in which the ruthenium (III) trichloride hydrate starting material is reacted with a large (in general 15- to 20-fold) excess of the appropriate ligand in the presence of zinc dust as reducing agent. The product can be obtained only in unsatisfactory yields and is highly contaminated, so that it has to be subjected to complicated purification. This process is unsuitable for industrial use.

EP 1 283 843B1 and EP 1 156 055A1 disclose a further process for preparing bis(2,4-dimethylpentadienyl)ruthenium(II), in which the starting compound dichloro(2,7-dimethylocta-2,6-diene-1,8-diyl)ruthenium(IV) is reacted with the appropriate ligand in the presence of a primary or secondary alcohol as reducing agent. The process has the disadvantage that the Ru(IV) starting compound has to be prepared in a complicated process. If the reduction does not proceed quantitatively, residues of Ru(III) or Ru(IV) and also polymeric components can remain. The yields are reduced by a sublimation which is necessary. As a result, the overall process is expensive and hardly suitable for industrial use.

G. L. D. Ritchie et al. (*J. Am. Chem. Soc.*, Vol. 105, No. 16, 1983, pp. 5215-5219) describe a process for preparing closed, "classical" ruthenocenes, in particular biscyclopentadienyl-ruthenium(II). The process is a two-stage process. In the first stage, cyclopentadienyl-sodium (Na-Cp) is prepared from fresh cyclopentadiene and metallic sodium, and this functions as ligand transfer agent. In the second stage, the dichloro (tetrakis(dimethyl sulphoxide))ruthenium(II) starting material is reacted with cyclopentadienylsodium. A disadvantage of this process is the use of cyclopentadienyl-sodium which is very air- and moisture-sensitive, so that special reaction conditions (protective gas technique, nitrogen-saturated and dry solvents) are necessary. The process is therefore complicated and expensive and not very suitable for industrial use. In addition, this process cannot readily be applied to the preparation of open dienyl-Ru complexes since the sodium salts of the corresponding open dienyls are difficult to obtain.

It was therefore an object of the present invention to provide a process for preparing dienyl-ruthenium complexes, in particular open ruthenocenes, which is suitable for economical, industrial use and gives products in high purity and high yield. Furthermore, the process should be a single-stage process, be based on starting compounds which are simple to prepare and avoid the use of sensitive, organometallic bases.

This object is achieved according to the invention by provision of the process according to claim 1.

The present invention relates to a process for preparing dienyl-ruthenium complexes of the formula

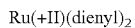

characterized in that a ruthenium starting compound of the formula

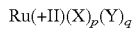

where
  X=an anionic group,
  Y=an uncharged two-electron donor ligand,
  p=an integer from 1 to 2,
  q=an integer from 1 to 6,
is reacted with a diene ligand L in the presence of an inorganic and/or organic base in a single-stage process. Further preferred embodiments of the process are characterized in the dependent claims.

The reaction of the diene ligand L with the inorganic and/or organic base to form the (dienyl)$_2$-ruthenium complex is carried out in a single-stage process. The generation of the dienyl anion L$^-$ from the diene ligand L is carried out in the presence of the ruthenium(II) starting compound. A separate preparation of the dienyl anion L$^-$ in a preceding step is therefore dispensed with. The use of sensitive organometallic bases for deprotonating the diene ligand (or for producing the dienyl anion L$^-$) is likewise dispensed with.

After the reaction, the two diene ligands L are present in anionic form (as dienyl anion L$^-$) in the ruthenium complex, so that together with the central Ru atom bearing two positive charges they form an electrically neutral dienyl complex of the formula Ru(+II)(dienyl)$_2$. Since the oxidation state of the Ru atom in the starting compound Ru(+II)(X)$_p$(Y)$_q$ and in the Ru(+II)(dienyl)$_2$ complex remains constant (i.e. +II), no reducing agent is needed.

For the purposes of the present invention, diene ligands L are ligands which have at least two unsaturated groups of the type >C=X (where X=CR$_2$, O, S, NR) in their molecular structure, with at least one of these groups representing a >C=C<double bond. Deprotonation of the diene ligand L according to the invention forms an anion L$^-$ in which the negative charge is distributed over a conjugated π-electron system. In the preferred embodiment, this conjugated π-electron system is a nonaromatic system.

As diene ligands L, it is possible to use either cyclic or open-chain dienes which can in each case be monosubstituted or polysubstituted. Mixtures and combinations of various diene ligands can also be used. Permissible substituents on the diene ligands encompass halogen atoms, alkyl groups, acyl groups, alkoxy groups, alkoxycarbonyl groups, silyl groups, stannyl groups, amine groups and imine groups. Examples of suitable diene ligands L are:

- substituted or unsubstituted open-chain pentadienes such as 1,3-pentadiene, 2,4-dimethyl-1,3-pentadiene, 2,4-dimethyl-1,4-pentadiene, 2,3,4-trimethyl-1,3-pentadiene, 3-phenyl-1,3-pentadiene, 2-methyl-1,3-pentadiene or 3-(trimethyl-silyl)-1,3-pentadiene,
- substituted or unsubstituted open-chain hexadienes or heptadienes,
- heteroatom-substituted dienes or diene analogues such as mesityl oxide (2-methyl-4-oxo-2-pentene) or (N-3-buten-1-ylidene)methanamine,
- substituted or unsubstituted cyclic dienes such as cyclohexadiene, cycloheptadiene or cyclooctadiene,
- substituted or unsubstituted cyclic dienes such as cyclopentadienes, fluorenes or indenes which after deprotonation form an aromatic π-electron system.

Combinations of the individual diene ligands are also possible in the process of the invention. They lead to the preparation of dienyl-Ru(II) complexes having different dienyl ligands.

The typical amounts of the diene ligand L or the diene ligand mixture added are from 1 to 4 equivalents, preferably from 2 to 3 equivalents and particularly preferably from 2 to 2.5 equivalents, in each case based on the ruthenium complex. When two different diene ligands are used, the total amount added is divided in a suitable ratio, and the addition can then be carried out in parallel or in succession.

A possible explanation for the surprising course of the reaction is that the diene ligands L firstly coordinate in uncharged form to the ruthenium. This weakens a C—H bond of the diene ligand (presumably by means of an "agostic interaction") so that even a relatively weak inorganic or organic base can easily deprotonate this bond. After the reaction, the diene ligands L are formally present in singly negatively charged form (as dienyl anion L$^-$).

The coordination of the diene ligands L to the central Ru atom is promoted by the presence of the uncharged two-electron donor ligands Y. According to the invention, a ruthenium starting compound of the formula Ru(+II)(X)$_p$(Y)$_q$, where the Ru is present in the oxidation state +II, X is an anionic group, Y is an uncharged two-electron donor ligand and p is an integer from 1 to 2 and q is an integer from 1 to 6, is used. Examples of uncharged two-electron donor ligands Y are NH$_3$, amines and, in particular, solvent molecules such as acetonitrile, water, THF, dioxane, DMSO (dimethyl sulphoxide), DMF (dimethylformamide), acetone, pyridine, benzonitrile or acrylonitrile. The ruthenium starting compound can also have mixtures and combinations of various donor ligands Y.

Examples of the anionic group X in the ruthenium starting compound are monoanions such as halides (e.g. F$^-$, Cl$^-$, Br$^-$, I$^-$), pseudohalides (e.g. CN$^-$, CNO$^-$, SCN$^-$), trifluoromethylsulphonate anions (CF$_3$SO$_3^-$) and nitrates, perchlorates, acetates or trifluoroacetates. However, the anionic group X can also encompass dianions such as sulphate ions (SO$_4^{2-}$).

Examples of suitable starting compounds of the type Ru(+II)(X)$_p$(Y)$_q$ are RuCl$_2$(acetonitrile)$_4$, RuBr$_2$(acetonitrile)$_4$, RuCl$_2$(pyridine)$_4$, [Ru(H$_2$O)$_6$]Cl$_2$, [Ru(H$_2$O)$_6$](triflate)$_2$, [Ru(H$_2$O)$_2$](acetate)$_2$, RuCl$_2$(DMSO)$_4$, [Ru(NH$_3$)$_6$]Cl$_2$, RuCl$_2$(benzonitrile)$_4$. Such compounds are known to those skilled in the art and can be prepared by literature methods (cf., for example, W. E. Newton and J. E. Searles, *Inorganica Chimica Acta*, 1973, 3, pp. 349-352 or F. M. Lever, A. R. Powell, *J. Chem. Soc.* (A), 1969, pp. 1477-1482). Some of these starting compounds are also available from various suppliers.

In a preferred embodiment of the process of the invention, the Ru starting compound can also be prepared "in-situ" and be used directly without intermediate isolation (cf. the "one-pot process" in Examples 8, 11 and 12). This variant is particularly time-saving and inexpensive since simple, readily available starting compounds (for example ruthenium(III) chloride) are used.

As bases, use is made of inorganic and/or organic bases. Examples of inorganic bases are alkali metal or alkaline earth metal hydroxides such as NaOH, KOH or Ca(OH)$_2$, alkali metal or alkaline earth metal carbonates such as lithium carbonate (Li$_2$CO$_3$), sodium carbonate (Na$_2$CO$_3$), sodium hydrogencarbonate (NaHCO$_3$) or calcium carbonate (CaCO$_3$), alkali metal or alkaline earth metal phosphates such as Na$_3$PO$_4$ and also basic oxides such as calcium oxide (CaO) or aluminium oxide (Al$_2$O$_3$).

Examples of organic bases are ammonia, diethylamine, trimethylamine, triethylamine, urotropin, ethanolamine, pyridine, triethanolamine, DBU (1,8-diaza-bicyclo[5.4.0]undec-7-ene), DBN (diazabicyclononane), DABCO (1,4-diazabicyclo[2.2.2]octane), imidazole and ethylenediamine. It is also possible to use mixtures of the organic and inorganic bases mentioned. Preference is given to inorganic bases, in particular lithium carbonate (Li$_2$CO$_3$) and sodium carbonate (Na$_2$CO$_3$). The amounts of base added are from 1 to 10 equivalents, preferably from 2 to 5 equivalents, in each case based on the Ru complex.

Other bases, in particular organometallic bases, which have a carbanion (for example n-butyllithium, methyllithium, tert-butyllithium, Na-cyclopentadienide or Grignard reagents) are not used. Owing to their sensitivity, for example towards water, they are unsuitable for the conditions of the process of the invention.

The process of the present invention can in principle be carried out in all customary polar organic solvents. Use is made here of polar organic solvents from the class of alcohols, ketones, ethers, amides or esters. Examples of suitable polar organic solvents are ethanol, acetone, THF, dimethylformamide (DMF) or dioxane and also mixtures thereof. The organic solvents do not have to be dried before use. The process is preferably carried out in a mixture of a polar organic solvent with water (i.e. in an aqueous solvent mixture). Examples of suitable mixtures of a polar organic solvent with water are isopropanol/water, ethanol/water, acetone/water, THF/water and dioxane/water, in each case using deionized water. The volume-based mixing ratio of polar organic solvent/deionized water is in the range from 1:20 to 20:1, preferably in the range from 1:10 to 10:1 and particularly preferably in the range from 1:5 to 5:1.

The reaction according to the invention is carried out at temperatures in the range from −30 to 120° C., preferably from 20 to 100° C. and particularly preferably under reflux.

To carry out the process, the Ru(+II) starting compound (e.g. prepared according to the literature method described above) is initially charged in a polar organic solvent or in an aqueous solvent mixture.

The appropriate diene ligand or diene ligand mixture and the base are then added a little at a time. The mixture is heated for from 0.5 to 10 hours, preferably from 2 to 5 hours, at temperatures in the range from −30 to 120° C., preferably under reflux, and then cooled. The product can subsequently be extracted with nonpolar organic solvents such as hexane, pentane, cyclohexane or toluene. After taking off the solvent, the product obtained in this way is dried. In an alternative work-up step, the product can also be precipitated from the reaction mixture by addition of a polar protic solvent (e.g. water or ethylene glycol), then separated off by filtration and subsequently dried.

In a further embodiment of the process of the invention, the Ru starting compound is prepared in a preceding step ("in-situ") and is used directly without intermediate isolation in the process of the invention (cf. the "one-pot" process in Examples 8, 11 and 12). Here, the preparation of the Ru starting compound of the type $Ru(+II)(X)_p(Y)_q$ is combined with the preparation of the dienyl-Ru complex. This variant is particularly time-saving and inexpensive since simple, readily available ruthenium salts (for example ruthenium(III) chloride) are used. However, due to the reduction step for preparing the Ru(II) starting compound, protective gas has to be employed here.

It has surprisingly been found that the process of the invention gives the dienyl-Ru(II) complexes in high purity and very good yield. In general, yields in the range from 60 to 95% can be achieved. Owing to the use of the Ru(II) starting compound which contains uncharged two-electron donor ligands or solvent molecules, ligand replacement by the diene ligands L occurs under very mild conditions and virtually quantitatively.

Since the process uses water-insensitive, air-stable inorganic and/or organic bases, measures for making the system inert (protective gas, etc.) can generally be avoided. Furthermore, it is possible to use environmentally friendly aqueous solvent mixtures. For this reason, the process of the invention is particularly suitable for industrial conditions.

The purity of the dienyl-Ru compounds after extraction or precipitation is above 95%, preferably above 98% and particularly preferably above 99%. To achieve a high purity, the product can be subjected to a sublimation step. This makes it possible to achieve purities of over 99.8%.

The follow examples illustrate the invention.

EXAMPLE 1

Preparation of bis(2,4-dimethyl-1,3-pentadienyl)ruthenium(II) using $Li_2CO_3$ as base in isopropanol/water (2:1)

Formula:

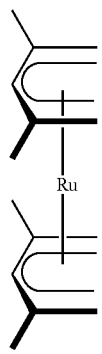

$RuCl_2(CH_3CN)_4$ (prepared by a literature method (Newton et al., see above); 20 g, 59.5 mmol) and $Li_2CO_3$ (base, 17.5 g, 238 mmol, 4 equivalents) are placed in a flask. Isopropanol (200 ml), deionized water (100 ml) and 2,4-dimethyl-1,3-pentadiene (from Aldrich; 14.3 g, 149 mmol, 2.5 equivalents) are added. The suspension is brought to reflux (90° C. oil bath temperature).

After one hour, another equivalent of the diene 2,4-dimethyl-1,3-pentadiene (5.7 g) is added. The light-brown mixture is stirred under reflux for another three hours (total 4 h under reflux) and then cooled to room temperature. The reaction mixture is extracted with n-hexane until the extract is colourless. The combined organic phases are washed with water and filtered through a filter aid (Celite). The clear yellow solution is evaporated on a rotary evaporator and the light-yellow product obtained is dried to constant weight at room temperature under reduced pressure.

Yield: 15 g=87%.

Purity determination by means of $^1$H-NMR: 98.6%.

Melting point: 105° C.

$^1$H-NMR (CDCl$_3$), δ(ppm): 0.61 (s br, 4H, CH$_2$), 1.9 (s, 12H, CH$_3$), 2.6 (s, br, 4H, CH$_2$), 4.9 (s, 2H, CH).

$^{13}$C-NMR (CDCl$_3$), δ(ppm): 26.3 (s, CH$_3$), 45.8 (s, br, CH$_2$), 97.8 (s, CH), 100.3 (s, C).

EXAMPLE 2

Preparation of bis(2,4-dimethyl-1,3-pentadienyl)ruthenium(II) using triethylamine (NEt$_3$) as base in isopropanol/water (2:1)

$RuCl_2(CH_3CN)_4$ (20 g, 59.5 mmol) is placed in a flask. Isopropanol (200 ml), water (100 ml), NEt$_3$ (19.9 g, 196 mmol, 3.3 equivalents) and 2,4-dimethyl-1,3-pentadiene (14.3 g, 149 mmol, 2.5 equivalents) are added. The suspension is brought to reflux (90° C. oil bath temperature). After one hour, another equivalent of 2,4-dimethyl-1,3-pentadiene (5.7 g) is added. The light-brown mixture is stirred under reflux for another three hours (total of 4 h under reflux) and then cooled to room temperature. The reaction mixture is extracted with n-hexane until the extract is colourless.

The combined organic phases are washed with water and filtered through Celite. The clear yellow solution is evaporated on a rotary evaporator and the crystalline light-yellow product obtained is dried to constant weight at room temperature under reduced pressure.

Yield: 14.4 g=83%.

EXAMPLE 3

Preparation of bis(2,4-dimethyl-1,3-pentadienyl)ruthenium(II) using $Na_2CO_3$ as base in isopropanol/water (2:1)

$RuCl_2(CH_3CN)_4$ (10 g, 29.7 mmol) and $Na_2CO_3$ (12.6 g, 119 mmol, 4 equivalents) is placed in a flask. Isopropanol (100 ml), deionized water (50 ml) and 2,4-dimethyl-1,3-pentadiene (10 g, 104 mmol, 3.5 equivalents) are added. The suspension is brought to reflux (95° C. oil bath temperature), stirred under reflux for four hours and then cooled to room temperature. The reaction mixture is extracted with n-hexane until the extract is colourless. The combined organic phases are washed with water and filtered through Celite. The clear yellow solution is evaporated on a rotary evaporator and the crystalline light-yellow product obtained is dried to constant weight at room temperature under reduced pressure.

Yield: 7.2 g, 84%.

EXAMPLE 4

Preparation of bis(2,4-dimethyl-1,3-pentadienyl)ruthenium(II) using triethylamine (NEt$_3$) as base in dioxane/water (2:1)

RuCl$_2$(CH$_3$CN)$_4$ (10 g, 29.7 mmol) is placed in a flask. Dioxane (100 ml), deionized water (50 ml), NEt$_3$ (8.4 ml, 60 mmol, 2 equivalents) and 2,4-dimethyl-1,3-pentadiene (12 g, 90 mmol, 3 equivalents) are added. The suspension is brought to reflux (110° C. oil bath temperature). The light-brown mixture is stirred under reflux for three hours and then cooled to room temperature. The reaction mixture is extracted with n-hexane until the extract is colourless. The combined organic phases are washed with water and filtered through Celite. The clear yellow solution is evaporated on a rotary evaporator and the crystalline light-yellow product obtained is dried to constant weight at room temperature under reduced pressure.

Yield: 5.8 g, 67%.

EXAMPLE 5

Preparation of bis(cycloheptadienyl)ruthenium(II) using Li$_2$CO$_3$ as base in isopropanol/water (1:1)

Formula:

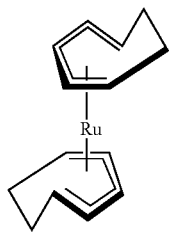

RuCl$_2$(CH$_3$CN)$_4$ (4 g, 12 mmol) and Li$_2$CO$_3$ (3.5 g, 47 mmol, 4 equivalents) are placed in a flask. Isopropanol (60 ml), water (60 ml) and cycloheptadiene (from Aldrich, 5 ml, 45 mmol, 3.8 equivalents) are added. The suspension is brought to reflux (90° C. oil bath temperature). The light-brown mixture is stirred under reflux for four hours and then cooled to room temperature. The reaction mixture is extracted with n-hexane until the extract is colourless. The combined organic phases are washed with water and dried over MgSO$_4$ and then filtered. The clear yellow solution is evaporated on a rotary evaporator and the crystalline light-yellow product obtained is dried to constant weight at room temperature under reduced pressure.

Yield: 2.96 g, 87%.

$^1$H-NMR (CD$_2$Cl$_2$), δ (ppm): 1.4 (m, 4H, CH$_2$), 1.9 (m, 4H, CH$_2$), 3.8 (m, 4H, CH), 4.45 (m, 4H, CH), 5.18 (m, 2H, CH).

EXAMPLE 6

Preparation of bis(2,4-dimethyl-1,3-pentadienyl)ruthenium(II) from RuCl$_2$(DMSO)$_4$ using NEt$_3$ as base in isopropanol/water An Ru(II)-dimethyl sulphoxide complex is used as ruthenium(II) starting compound. RuCl$_2$(DMSO)$_4$ (from Strem; 6.18 g, 12.5 mmol) is placed in a flask. Isopropanol (100 ml), deionized water (15 ml), NEt$_3$ (4.5 ml, 31 mmol, 2.5 equivalents) and 2,4-dimethyl-1,3-pentadiene (6 ml, 44 mmol, 3.5 equivalents) are added. The suspension is brought to reflux (90° C. oil bath temperature). The solid dissolves completely and the solution becomes red and then orange. The solution is stirred under reflux for a total of four hours and then cooled to room temperature. Deionized water is added to precipitate the product. The precipitated crystalline light-yellow product is filtered off, washed with water and dried to constant weight at room temperature under reduced pressure.

Yield: 1.6 g, 44%. The analytical data agree with those reported in Example 1.

EXAMPLE 7

Preparation of bis(η$^5$-2,4-dimethyl-1-oxapentadienyl)ruthenium(II)

Formula:

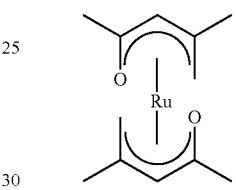

RuCl$_2$(CH$_3$CN)$_4$ (10 g, 30 mmol) and Li$_2$CO$_3$ (8.7 g, 118 mmol, 4 eq.) are placed in a flask. Isopropanol (200 ml), water (100 ml) and mesityl oxide (18.7 ml, 148 mmol, 5 eq.) are added. The suspension is made inert using protective gas and brought to reflux (90° C. oil bath temperature). The light-brown mixture is stirred under reflux for four hours and then cooled to room temperature. The work-up is continued in air. The reaction mixture is extracted with n-hexane until the extract is colourless. The combined organic phases are washed once with water and dried over MgSO$_4$, then filtered. The clear yellow solution is evaporated on a rotary evaporator and the light-brown crystalline product obtained is dried to constant weight at room temperature under reduced pressure.

Yield as mixture of two isomers: 4.4 g, 50%.

EXAMPLE 8

Preparation of bis(2,4-dimethyl-1,3-pentadienyl)ruthenium(II) in a one-pot process RuCl$_3$ hydrate (from Umicore Hanau, 37.8% of Ru, 20 g, 74.8 mmol) is placed in a flask and dissolved in EtOH (200 ml) and DMF (dimethylformamide, 50 ml). The suspension is made inert using protective gas and reduced to Ru(II)Cl$_2$(DMF)$_n$ (n~4) by means of a reducing agent (e.g. hydrogen/Pt black or hydrazine). Triethylamine (49 ml, 5 eq.) and 2,4-dimethyl-1,3-pentadiene (29 ml, 224 mmol, 3 eq.) are added to the resulting dark-green solution. The mixture is stirred at room temperature for another 10 hours and water (400 ml) is subsequently added. The product precipitates in the form of light-yellow crystals, and these are filtered off, washed with water and dried to constant weight under reduced pressure.

Yield: 14 g, 65%.

EXAMPLE 9

Preparation of bis(pentamethylcyclopentadienyl)ruthenium(II) using $Li_2CO_3$ as base in isopropanol/water (2:1)

Formula:

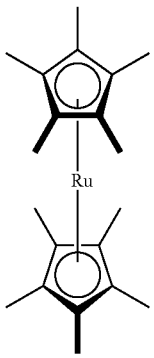

$RuCl_2(CH_3CN)_4$ (10 g, 30 mmol) and $Li_2CO_3$ (8.7 g, 118 mmol, 4 equivalents) are placed in a flask. Isopropanol (200 ml), deionized water (100 ml) and pentamethyl-cyclopentadiene (from Aldrich, 12.8 g, 88 mmol, 3 equivalents) are added. The suspension is brought to reflux (90° C. oil bath temperature). The light-brown mixture is stirred under reflux for four hours and then cooled to room temperature.

Deionized water is then added; the precipitated product is filtered off and washed with cold ethanol. The white crystalline product obtained is dried to constant weight at room temperature under reduced pressure.

Yield: 10.9 g, quantitative.

$^1$H-NMR ($CD_2Cl_2$), δ (ppm): 1.54 (s, $CH_3$).

EXAMPLE 10

Preparation of bis(2,4-dimethyl-1,3-pentadienyl)ruthenium(II) using $Na_2CO_3$ as base in acetone/water (3:1)

$RuCl_2(CH_3CN)_4$ (10 g, 30 mmol) and $Na_2CO_3$ (12.6 g, 119 mmol, 4 equivalents) is placed in a flask. Acetone (100 ml), deionized water (30 ml) and 2,4-dimethyl-1,3-pentadiene (10 g, 104 mmol, 3.5 equivalents) are added. The suspension is brought to reflux (65° C. oil bath temperature) and stirred under reflux for five hours, then cooled to room temperature. The reaction mixture is extracted with n-hexane until the extract is colourless. The combined organic phases are washed with water, dried over $MgSO_4$ and filtered through Celite. The clear yellow solution is evaporated on a rotary evaporator and the crystalline light-yellow product obtained is dried to constant weight at room temperature under reduced pressure.

Yield: 7.9 g, 91%.

EXAMPLE 11

Preparation of bis(2,4-dimethyl-1,3-pentadienyl)ruthenium(II) in a one-pot process in ethanol/acetonitrile with $Na_2CO_3$ as base $RuCl_3$ hydrate (from Umicore Hanau, 40.13% of Ru, 40 g, 159 mmol) is placed in a flask and dissolved in EtOH (500 ml), deionized water (200 ml) and acetonitrile (34 ml, 4 eq.). The mixture is made inert using protective gas and reduced to $Ru(II)Cl_2(CH_3CN)_4$ by means of a reducing agent (e.g. hydrogen/Pt black or hydrazine). 2,4-Dimethyl-1,3-pentadiene (72 ml, 556 mmol, 3.5 eq.) and $Na_2CO_3$ (67 g, 4 eq.) are added to the resulting yellow-orange solution of $RuCl_2(CH_3CN)_4$. The suspension is brought to reflux (85° C. oil bath temperature) and stirred under reflux for three hours, then cooled to room temperature. Deionized water (300 ml) is subsequently added. The product precipitates as light-yellow crystals. These are filtered off, washed with water and dried to constant weight under reduced pressure. The product can be further purified by dissolving it in n-hexane or toluene, treating it with activated carbon and filtering the solution through Celite, silica gel or alumina. The resulting clear yellow solution is evaporated to dryness on a rotary evaporator. The crystalline light-yellow product is dried at room temperature under vacuum.

Yield: 33 g, 71%.

EXAMPLE 12

Preparation of bis(2,4-dimethyl-1,3-pentadienyl)ruthenium(II) in a one-pot process in ethanol/acetonitrile with $Na_3PO_4$ as base $RuCl_3$ hydrate (from Umicore Hanau, 40.13% of Ru, 20 g, 79.4 mmol) is placed in a flask and dissolved in EtOH (200 ml), deionized water (50 ml) and acetonitrile (17 ml, 4 eq.). The mixture is made inert using protective gas and reduced to $Ru(II)Cl_2(CH_3CN)_4$ by means of a reducing agent (e.g. hydrogen/Pt black or hydrazine). 2,4-Dimethyl-1,3-pentadiene (36 ml, 278 mmol, 3.5 eq.) and $Na_3PO_4$ (68 g, 397 mmol, 5 eq.) are added to the resulting yellow-orange solution of $RuCl_2(CH_3CN)_4$. The suspension is brought to reflux (85° C. oil bath temperature) and stirred under reflux for four hours, then cooled to room temperature. Deionized water (400 ml) is subsequently added. The product precipitates as light-yellow crystals. These are filtered off, washed with water and dried to constant weight under reduced pressure. The product can be further purified by dissolving it in n-hexane or toluene, treating it with activated carbon and filtering the solution through Celite, silica gel or alumina. The resulting clear yellow solution is evaporated to dryness on a rotary evaporator. The crystalline light-yellow product is dried at room temperature under vacuum.

Yield: 18.3 g, 79%.

EXAMPLE 13

Preparation of bis(indenyl)ruthenium(II) using $Li_2CO_3$ as base in isopropanol/water (2:1)

Formula:

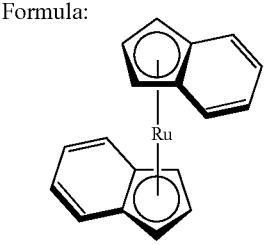

$RuCl_2(CH_3CN)_4$ (10 g, 30 mmol) and $Li_2CO_3$ (8.7 g, 118 mmol, 4 equivalents) are placed in a flask. Isopropanol (200 ml), deionized water (100 ml) and indene (from Aldrich, 7.3 g, 60 mmol, 2 equivalents) are added. The suspension is brought to reflux (90° C. oil bath temperature). The light-brown mixture is stirred under reflux for four hours and then cooled to room temperature. Deionized water is then added, the precipitated product is filtered off and washed with cold ethanol. The orange crystalline product obtained is dried to constant weight at room temperature under reduced pressure.

Yield: 4.8 g, 50%.

The NMR data are in agreement with the published ones.

The invention claimed is:

1. Process for preparing dienyl-ruthenium complexes of the formula

wherein a ruthenium starting compound of the formula

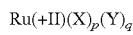

where
X=an anionic group,
Y=an uncharged two-electron donor ligand,
p=an integer from 1 to 2,
q=an integer from 1 to 6,
is reacted with a diene ligand L in the presence of an inorganic and/or organic base in a single-stage process.

2. Process according to claim 1, wherein the generation of the dienyl anion ($L^-$) from the diene ligand L is carried out in the presence of the ruthenium(II) starting compound.

3. Process according to claim 1, wherein the reaction is carried out in a polar organic solvent or in a mixture of a polar organic solvent with water.

4. Process according to claim 1, wherein the diene ligand L has at least two unsaturated groups of the type >C=X (where X=$CR_2$, O, S, NR) in its molecular structure and at least one of these groups represents a >C=C< double bond and after the reaction of the diene ligand L with the base a dienyl anion ($L^-$) is present, in which the negative charge is distributed over a conjugated π-electron system.

5. Process according to claim 1, wherein the diene ligand L is a cyclic diene and is selected from the group consisting of substituted or unsubstituted cyclopentadienes, fluorenes and indenes.

6. Process according to claim 1, wherein the negative charge of the dienyl anion ($L^-$) is distributed over a conjugated π-electron system which is a nonaromatic system.

7. Process according to claim 6, wherein the diene ligand L is an open diene and is selected from the group of substituted or unsubstituted pentadienes, hexadienes and heptadienes.

8. Process according to claim 6, wherein the diene ligand L is a cyclic diene and is selected from the group of substituted or unsubstituted cyclohexadienes, cycloheptadienes or cyclooctadienes.

9. Process according to claim 6, wherein the diene ligand L is a heteroatom-substituted diene analogue and comprises mesityl oxide (2-methyl-4-oxo-2-pentene) or (N-3-buten-1-ylidene)-methanamine.

10. Process according to claim 6, wherein the diene ligand L is selected from the group of 1,3-pentadiene, 2,4-dimethyl-1,3-pentadiene, 2,4-dimethyl-1,4-pentadiene, 2,3,4-trimethyl-1,3-pentadiene, 3-phenyl-1,3-pentadiene, 2-methyl-1,3-pentadiene or 3-(trimethylsilyl)-1,3-pentadiene and mixtures thereof.

11. Process according to claim 1, wherein the amount of the diene ligand added is from 1 to 4 equivalents based on the Ru starting compound.

12. Process according to claim 1, wherein alkali metal or alkaline earth metal hydroxides, alkali metal or alkaline earth metal carbonates, alkali metal or alkaline earth metal hydrogencarbonates, alkali metal or alkaline earth metal phosphates, or basic oxides or mixtures thereof are used as inorganic base.

13. Process according to claim 1, wherein ammonia, diethylamine, trimethylamine, triethylamine, urotropin, ethanolamine, pyridine, triethanol-amine, DBU (1,8-diazabicyclo[5.4.0]undec-7-ene), DBN (diazabicyclononane), DABCO (1,4-diazabicyclo[2.2.2]octane), imidazole or ethylenediamine or a mixture thereof is used as organic base.

14. Process according to claim 1, wherein the amount of the inorganic and/or organic base added is from 1 to 10 equivalents, based on the ruthenium compound).

15. Process according to claim 1, wherein the uncharged two-electron donor ligand Y of the Ru(II) starting compound is selected from acetonitrile, water, tetrahydrofuran, dioxane, dimethyl sulphoxide, acetone, pyridine, benzonitrile, benzyl nitrile, acrylonitrile, isonitrile, ammonia or an amine group.

16. Process according to claim 1, wherein the anionic group X of the ruthenium(II) starting compound is selected from halide ions, pseudohalide ions, sulphate ions ($SO_4^{2-}$), trifluoromethylsulphonate anions ($CF_3SO_3^-$), nitrates, perchlorates, acetates or trifluoroacetates.

17. Process according to claim 1, wherein the ruthenium (II) starting compound is selected from the group of $RuCl_2$(acetonitrile)$_4$, $RuBr_2$(acetonitrile)$_4$, $RuCl_2$(pyridine)$_4$, [Ru($H_2O$)$_6$]$Cl_2$, [Ru($H_2O$)$_6$] (triflate)$_2$, $RuCl_2$(DMSO)$_4$, [Ru($NH_3$)$_6$]$Cl_2$, $RuCl_2$(benzonitrile)$_4$ or $RuCl_2$(acrylonitrile)$_4$.

18. Process according to claim 1, wherein the dienyl-ruthenium complex is precipitated from the reaction mixture by addition of a polar protic solvent.

19. Process according to claim 1, wherein the Ru(II) starting compound is prepared in a preceding step and is used directly without intermediate isolation in the process ("one-pot process").

20. A method for producing a homogeneous catalyst comprising: introducing dienyl-ruthenium complex prepared according to claim 1 as a precursor.

* * * * *